(12) United States Patent
Moffitt et al.

(10) Patent No.: US 10,350,413 B2
(45) Date of Patent: *Jul. 16, 2019

(54) SYSTEMS, METHODS, AND VISUALIZATION TOOLS FOR STIMULATION AND SENSING OF NEURAL SYSTEMS WITH SYSTEM-LEVEL INTERACTION MODELS

(71) Applicant: Boston Scientific Neuromodulation Corporation, Valencia, CA (US)

(72) Inventors: Michael A. Moffitt, Saugus, CA (US); Rafael Carbunaru, Valley Village, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 347 days.

This patent is subject to a terminal disclaimer.

(21) Appl. No.: 15/408,205

(22) Filed: Jan. 17, 2017

(65) Prior Publication Data

US 2017/0120054 A1 May 4, 2017

Related U.S. Application Data

(63) Continuation of application No. 14/538,066, filed on Nov. 11, 2014, now Pat. No. 9,586,053.
(Continued)

(51) Int. Cl.
*A61N 1/00* (2006.01)
*A61N 1/36* (2006.01)
(Continued)

(52) U.S. Cl.
CPC ....... *A61N 1/36135* (2013.01); *A61N 1/0534* (2013.01); *A61N 1/3605* (2013.01);
(Continued)

(58) Field of Classification Search
CPC ............ A61N 1/36025; A61N 1/36135; A61N 1/3605; A61N 1/0534; A61N 1/36185;
(Continued)

(56) References Cited

U.S. PATENT DOCUMENTS

| 5,099,846 A | 3/1992 | Hardy |
| 5,361,763 A | 11/1994 | Kao et al. |

(Continued)

FOREIGN PATENT DOCUMENTS

| WO | 01/58520 | 8/2001 |
| WO | 2001/090876 A1 | 11/2001 |

(Continued)

OTHER PUBLICATIONS

European Patent Office, International Searching Authority, International Search Report and the Written Opinion of the ISA in International Application No. PCT/US2011/040329, dated Dec. 29, 2011, 14 pages.

(Continued)

*Primary Examiner* — Mallika D Fairchild
(74) *Attorney, Agent, or Firm* — Lowe Graham Jones PLLC; Bruce E. Black

(57) ABSTRACT

A computer implemented system and method generates a patient-specific model of patient response to stimulation on a neural element basis, receives user-input of target neuromodulation sites, and, based on the patient-specific model, determines which stimulation paradigm and settings, including stimulation sites, would result in the target neuromodulation, where the stimulation sites are not necessarily the same as the resulting neuromodulation sites. The system outputs a visual representation of the stimulation sites that would result in the target neuromodulation. The system
(Continued)

monitors a system state and/or patient state and dynamically changes which stimulation program to implement based on the state.

12 Claims, 8 Drawing Sheets

Related U.S. Application Data

(60) Provisional application No. 62/058,131, filed on Oct. 1, 2014, provisional application No. 61/904,248, filed on Nov. 14, 2013.

(51) Int. Cl.
  *A61N 1/372* (2006.01)
  *A61N 1/05* (2006.01)

(52) U.S. Cl.
  CPC ..... *A61N 1/36185* (2013.01); *A61N 1/37264* (2013.01); *A61N 1/36025* (2013.01)

(58) Field of Classification Search
  CPC ............ A61N 1/37264; A61N 1/36128; A61N 1/36082; A61N 1/37247
  See application file for complete search history.

(56) References Cited

U.S. PATENT DOCUMENTS

| | | |
|---|---|---|
| 5,452,407 A | 9/1995 | Crook |
| 5,724,985 A | 3/1998 | Snell et al. |
| 5,782,762 A | 7/1998 | Vining |
| 5,938,688 A | 8/1999 | Schiff |
| 6,066,163 A | 5/2000 | John |
| 6,083,162 A | 7/2000 | Vining |
| 6,106,460 A | 8/2000 | Panescu et al. |
| 6,240,308 B1 | 5/2001 | Hardy et al. |
| 6,289,239 B1 | 9/2001 | Panescu et al. |
| 6,310,619 B1 | 10/2001 | Rice |
| 6,319,241 B1 | 11/2001 | King et al. |
| 6,351,675 B1 | 2/2002 | Tholen et al. |
| 6,389,311 B1 | 5/2002 | Whayne et al. |
| 6,463,328 B1 | 10/2002 | John |
| 6,491,699 B1 | 12/2002 | Henderson et al. |
| 6,539,263 B1 | 3/2003 | Schiff et al. |
| 6,622,048 B1 | 9/2003 | Mann et al. |
| 6,690,972 B2 | 2/2004 | Conley et al. |
| 6,694,162 B2 | 2/2004 | Hartlep |
| 6,694,163 B1 | 2/2004 | Vining |
| 6,748,098 B1 | 6/2004 | Rosenfeld |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,909,913 B2 | 6/2005 | Vining |
| 7,003,349 B1 | 2/2006 | Andersson et al. |
| 7,003,352 B1 | 2/2006 | Whitehurst |
| 7,008,370 B2 | 3/2006 | Tanner et al. |
| 7,035,690 B2 | 4/2006 | Goetz |
| 7,043,293 B1 | 5/2006 | Baura |
| 7,050,857 B2 | 5/2006 | Samuelsson et al. |
| 7,107,102 B2 | 9/2006 | Daignault, Jr. et al. |
| 7,136,518 B2 | 11/2006 | Griffin et al. |
| 7,136,695 B2 | 11/2006 | Pless et al. |
| 7,146,219 B2 | 12/2006 | Sieracki et al. |
| 7,146,223 B1 | 12/2006 | King |
| 7,151,961 B1 | 12/2006 | Whitehurst et al. |
| 7,155,279 B2 | 12/2006 | Whitehurst et al. |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,209,787 B2 | 4/2007 | DiLorenzo |
| 7,216,000 B2 | 5/2007 | Sieracki et al. |
| 7,217,276 B2 | 5/2007 | Henderson et al. |
| 7,218,968 B2 | 5/2007 | Condie et al. |
| 7,231,254 B2 | 6/2007 | DiLorenzo |
| 7,239,910 B2 | 7/2007 | Tanner |
| 7,239,926 B2 | 7/2007 | Goetz |
| 7,242,984 B2 | 7/2007 | DiLorenzo |
| 7,252,090 B2 | 8/2007 | Goetz |
| 7,254,446 B1 | 8/2007 | Erickson et al. |
| 7,257,447 B2 | 8/2007 | Cates et al. |
| 7,266,412 B2 | 9/2007 | Stypulkowski |
| 7,295,876 B1 | 11/2007 | Erickson |
| 7,313,430 B2 | 12/2007 | Urquhart et al. |
| 7,324,851 B1 | 1/2008 | DiLorenzo |
| 7,346,382 B2 | 3/2008 | McIntyre et al. |
| 7,388,974 B2 | 6/2008 | Yanagita |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,603,177 B2 | 10/2009 | Sieracki et al. |
| 7,617,002 B2 | 11/2009 | Goetz |
| 7,623,918 B2 | 11/2009 | Goetz |
| 7,657,319 B2 | 2/2010 | Goetz et al. |
| 7,676,273 B2 | 3/2010 | Goetz et al. |
| 7,734,340 B2 | 6/2010 | De Ridder |
| 7,826,902 B2 | 11/2010 | Stone et al. |
| 7,848,802 B2 | 12/2010 | Goetz et al. |
| 8,180,601 B2 | 5/2012 | Butson et al. |
| 8,452,415 B2 | 5/2013 | Goetz et al. |
| 8,606,360 B2 | 12/2013 | Butson et al. |
| 8,620,452 B2 | 12/2013 | King et al. |
| 8,798,764 B2 | 8/2014 | Molnar et al. |
| 8,918,184 B1 | 12/2014 | Torgerson et al. |
| 2004/0034394 A1 | 2/2004 | Woods et al. |
| 2004/0044279 A1 | 3/2004 | Lewin et al. |
| 2004/0106916 A1 | 6/2004 | Quaid et al. |
| 2004/0199216 A1 | 10/2004 | Lee et al. |
| 2004/0267330 A1 | 12/2004 | Lee et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0171587 A1 | 8/2005 | Daglow et al. |
| 2005/0228250 A1 | 10/2005 | Bitter et al. |
| 2006/0017749 A1 | 1/2006 | McIntyre et al. |
| 2006/0020292 A1 | 1/2006 | Goetz et al. |
| 2006/0094951 A1 | 5/2006 | Dean et al. |
| 2006/0235472 A1 | 10/2006 | Goetz et al. |
| 2006/0259079 A1 | 11/2006 | King |
| 2007/0027514 A1 | 2/2007 | Gerber |
| 2007/0043268 A1 | 2/2007 | Russell |
| 2007/0049817 A1 | 3/2007 | Preiss et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0156186 A1 | 7/2007 | Lee et al. |
| 2007/0162086 A1 | 7/2007 | DiLorenzo |
| 2007/0185544 A1 | 8/2007 | Dawant et al. |
| 2007/0191912 A1 | 8/2007 | Fischer et al. |
| 2007/0197891 A1 | 8/2007 | Shachar et al. |
| 2007/0203450 A1 | 8/2007 | Berry |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0021292 A1 | 1/2008 | Stypulkowski |

(56) References Cited

U.S. PATENT DOCUMENTS

| | | |
|---|---|---|
| 2008/0027514 A1 | 1/2008 | DeMulling et al. |
| 2008/0071150 A1 | 3/2008 | Miesel et al. |
| 2008/0081982 A1 | 4/2008 | Simon et al. |
| 2008/0103533 A1 | 5/2008 | Patel et al. |
| 2008/0123922 A1 | 5/2008 | Gielen et al. |
| 2008/0123923 A1 | 5/2008 | Gielen et al. |
| 2008/0141217 A1 | 6/2008 | Goetz et al. |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0269588 A1 | 10/2008 | Csavoy et al. |
| 2008/0300654 A1 | 12/2008 | Lambert et al. |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0204192 A1 | 8/2009 | Carlton et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0135553 A1 | 6/2010 | Joglekar |
| 2010/0137944 A1 | 6/2010 | Zhu |
| 2010/0179562 A1 | 7/2010 | Linker et al. |
| 2011/0172737 A1 | 7/2011 | Davis et al. |
| 2011/0191275 A1 | 8/2011 | Lujan et al. |
| 2011/0224757 A1 | 9/2011 | Zdeblick et al. |
| 2011/0307032 A1 | 12/2011 | Goetz et al. |
| 2012/0265268 A1 | 10/2012 | Blum et al. |
| 2012/0302912 A1 | 11/2012 | Moffitt et al. |
| 2013/0030499 A1 | 1/2013 | Pouratian |
| 2013/0221961 A1 | 8/2013 | Liu |

FOREIGN PATENT DOCUMENTS

| | | |
|---|---|---|
| WO | 2004/019799 A2 | 3/2004 |
| WO | 2007/097859 A1 | 8/2007 |
| WO | 2007/097861 A1 | 8/2007 |
| WO | 2007/100427 A1 | 9/2007 |
| WO | 2007/100428 A1 | 9/2007 |
| WO | 2007/112061 A2 | 10/2007 |
| WO | 2009097224 A1 | 8/2009 |
| WO | 2010/120823 A2 | 10/2010 |
| WO | 2011/139779 A1 | 11/2011 |
| WO | 2011/159688 A2 | 12/2011 |

OTHER PUBLICATIONS

European Patent Office, International Searching Authority, International Search Report and the Written Opinion of the ISA in International Application No. PCT/US2012/069667, dated Feb. 27, 2013, 15 pages.

European Patent Office, International Searching Authority, Partial International Search Report of the ISA in International Application No. PCT/US2013/056981, dated May 6, 2014, 4 pages.

European Patent Office, International Search Report and the Written Opinion of the ISA in International Application No. PCT/US2013/056975, dated Feb. 20, 2014, 11 pages.

European Patent Office, International Search Report and the Written Opinion of the ISA in International Application No. PCT/US2013/056984, dated Dec. 10, 2013, 11 pages.

European Patent Office, International Search Report and the Written Opinion/ISA in International Patent Application No. PCT/US2013/056112, dated May 15, 2014, 14 pages.

European Patent Office, International Search Report in International Application No. PCT/US2012/053344, dated Nov. 26, 2012, 8 pages.

European Patent Office, International Search Report in International Application No. PCT/US2012/050181, dated Jan. 3, 2013, 7 pages.

Euopean Patent Office, International Search Report and the Written Opinion in International Application No. PCT/US2012/050170, dated Oct. 5, 2012, 15 pages.

European Patent Office, International Search Report in International Application No. PCT/US09/03017, dated Aug. 3, 2009, 7 pages.

European Patent Office, International Search report and Written Opinion in PCT application No. PCT/US12/050174, dated Mar. 6, 2013, 20 pages.

European Patent Office, International Search Report and Written Opinion in International Application No. PCT/US2012/050187, dated Feb. 27, 2013, 9 pages.

European Patent Office, International Search Report and Written Opinion in International Application No. PCT/US2012/030700, dated Feb. 27, 2013, 9 pages.

European Patent Office, International Search Report in International Application No. PCT/US09/03041, dated Aug. 20, 2009, 7 pages.

European Patent Office, International Search Report and the Written Opinion of the International Searching Authority in International Application No. PCT/US2012/050175, dated Oct. 26, 2012, 15 pages.

European Patent Office, International Search Report in International Application No. PCT/US09/03038, dated Oct. 8, 2009, 9 pages.

European Patent Office, International Search Report in International Application No. PCT/US09/03040, dated Aug. 13, 2009, 7 pages.

European Patent Office, International Search Report in International Application No. PCT/US09/03049, dated Jan. 26, 2010, 8 pages.

European Patent Office, partial International Search Report in International Application No. PCT/US2012/030701, dated Feb. 15, 2013, 7 pages.

European Patent Office, partial International Search Report in International Application No. PCT/US2012/030705, dated Mar. 6, 2013, 7 pages.

Butson et al., "Current Steering to Control the Volume of Tissue Activated During Deep Brain Stimulation," Brain Stimulation 1, 2008, pp. 7-15.

Butson et al., "Patient Specific Analysis of the volume of tissue activated during deep brain stimulation," NeuroImage, Academic Press, vol. 34, No. 2, Dec. 2, 2006, pp. 661-670.

Butson et al., "Role of Electrode Design on the Volume of Tissue Activated During Deep Brain Stimulation," Journal of Neural Engineering, Mar. 1, 2006, vol. 3, No. 1, pp. 1-8.

Butson et al., "StimExplorer: Deep Brain Stimulation Parameter Selection Software System," Acta Neurochirugica, Jan. 1, 2007, vol. 97, No. 2, pp. 569-574.

Carnevale, N.T., et al., "The Neuron Book," Cambridge, UK: Cambridge University Press (2006), 480 pages.

Chaturvedi, "Development of Accurate Computational Models for Patient-Specific Deep Brain Stimulation," Electronic Thesis or Dissertation, Jan. 2012, 162 pages.

Chaturvedi A., et al., "Patient-specific models of deep brain stimulation: Influence of field model complexity on neural activation predictions," Brain Stimulation, Elsevier, Amsterdam, NL, vol. 3, No. 2, Apr. 2010, pp. 65-77.

Commowick, Olivier et al., "Using Frankenstein's Creature Paradigm to Build a Patient Specific Atlas," Sep. 20, 2009, Medical Image Computing and Computer-Assisted Intervention, pp. 993-1000.

Cover, T.M. et al., "Elements of information theory," (1991) John Wiley & Sons, New York, NY, pp. 1-542.

(56) References Cited

OTHER PUBLICATIONS

Dice, Lee R., "Measures of the Amount of Ecologic Association Between Species," Ecology 26(3) (1945), pp. 297-302. doi:10.2307/1932409, http://jstor.org/stable/1932409.

Ericsson, A., et al., "Construction of a patient-specific atlas of the brain: Application to normal aging," Biomedical Imaging: From Nano to Macro, ISBI 2008, 5th IEEE International Symposium, May 14, 2008, pp. 480-483.

Frankemolle et al., "Reversing cognitive-motor impairments in Parkinson's disease patients using a computational modelling approach to deep brain stimulation programming" Brain 133 (2010), pp. 746-761.

Hubert, Lawrence, et al., "Comparing partitions," Journal of Classification 2(1) (1985), pp. 193-218, doi:10.1007/BF01908075.

Izad, Olivier, "Computationally Efficient Method in Predicating Axonal Excitation," Dissertation for Masters Degree, Department of Biomedical Engineering, Case Western Reserve University, May 2009, 144 pages.

Jaccard, Paul, "Étude comparative de la distribution florale dans une portion odes Aples et des Jura," Bulletin de la Société Vaudoise des Sciences Naturelles (1901), vol. 37, pp. 547-579.

Klein, A. et al., "Evaluation of 14 nonlinear deformation algorithms applied to human brain MRI registration," NeuroImage, Academic Press, Orlando, FL, vol. 46, No. 3. Jul. 2009, pp. 786-802.

Liliane Ramus et al., "Assessing selection methods in the context of multi-atlas based segmentation," Biomedical Imaging: From Nano to Macro, 2010 IEEE International Symposium, Apr. 14, 2010, pp. 1321-1324.

Lotjonen, J.M.P., et al., "Fast and robust multi-atlas segmentation of brain magnetic resonance images," NeuroImage, Academic Press, vol. 49, No. 3, Feb. 1, 2010, pp. 2352-2365.

McIntyre, C. C., et al., "Modeling the excitability of mammalian nerve fibers: influence of afterpotentials on the recovery cycle," J Neurophysiol, 87(2) (Feb. 2002), pp. 995-1006.

Meila, Marina, "Comparing Clusterings by the Variation of Information," Learning Theory and Kernel Machines (2003), pp. 173-187.

Miocinovic et al., "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Peterson, et al., "Predicting myelinated axon activation using spatial characteristics of the extracellular field," Journal of Neural Engineering, 8 (2011), 12 pages.

Rand, W.M., "Objective criteria for the evaluation of clustering methods," Journal of the American Statistical Association (American Statistical Association) 66 (336) (1971), pp. 846-850, doi:10.2307/2284239, http://jstor.org/stable/2284239.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Schmidt et al., "Sketching and Composing Widgets for 3D Manipulation," Eurographics, Apr. 2008, vol. 27, No. 2, pp. 301-310.

Shen, Kaikai, et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Siegel, Ralph M., et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Volkmann, J., et al., "Introduction to the programming of deep brain stimulators," Mov. Disord., vol. 17 (Suppl 3) (2002), pp. 181-187.

Warman, et al., "Modeling the Effects of Electric Fields on nerve Fibers: Determination of Excitation Thresholds," IEEE Transactions on Biomedical Engineering, vol. 39, No. 12 (Dec. 1992), pp. 1244-1254.

Wesselink, et al., "Analysis of Current Density and Related Parameters in Spinal Cord Stimulation," IEEE Transactions on Rehabilitation Engineering, vol. 6, No. 2, Jun. 1998, pp. 200-207.

International Search Report and Written Opinion for PCT/US2014/064966 dated Feb. 10, 2015.

Official Communication for U.S. Appl. No. 14/538,066 dated May 20, 2016.

Official Communication for U.S. Appl. No. 14/538,066 dated Feb. 11, 2016.

Official Communication for U.S. Appl. No. 14/538,066 dated Aug. 19, 2015.

SYSTEMS, METHODS, AND VISUALIZATION TOOLS FOR STIMULATION AND SENSING OF NEURAL SYSTEMS WITH SYSTEM-LEVEL INTERACTION MODELS

CROSS-REFERENCE TO RELATED APPLICATIONS

This application is a continuation of U.S. patent application Ser. No. 14/538,066 filed Nov. 11, 2014 which claims the benefit under 35 U.S.C. § 119(e) of U.S. Provisional Patent Application Ser. No. 62/058,131, filed Oct. 1, 2014 and U.S. Provisional Patent Application Ser. No. 61/904,248, filed Nov. 14, 2013, all of which are incorporated herein by reference.

FIELD OF THE INVENTION

Aspects of the present invention are directed to a system(s) and method(s) for sensing and anatomical stimulation by electrodes of an implanted leadwire, where the stimulation is programmable to be responsive to a sensed signal. Aspects of the present invention are directed to a system for generating a patient-specific interaction model, determining a relationship between stimulation paradigms, including stimulation sites, and neuromodulation sites, dynamically changing stimulation goals and paradigms in response to sensed changes to a state, and/or outputting visual representations of a correlation between candidate stimulation sites and affected anatomical regions. Aspects of the present invention are directed to a system configured to perform stimulations and sense or receive input of data concerning effects of the stimulations to generate a patient-specific interaction model usable by the system to determine the sites to be stimulated for causing neuromodulation at sites selected by a user and for outputting a visual mapping of relationships between candidate stimulation sites and the affected neuromodulation sites. Aspects of the present invention are directed to generating a patient-specific interaction model based on tractography analysis prior to implantation of a leadwire, the model indicating various relationships between candidate stimulation sites and the affected neuromodulation sites for different placements of the leadwire, the model being output for use by a user to pre-operatively determine an optimal implantation site for the leadwire. The system is usable both for clinical use, and for analysis and scientific investigation. The present invention is further related to subject matter of U.S. patent application Ser. No. 13/160,104, which published as U.S. Pat. App. Pub. No. 2012/0014580, the entire content of which is hereby incorporated by reference herein in its entirety.

BACKGROUND INFORMATION

Stimulation of anatomical regions of a patient is a clinical technique for the treatment of disorders. Such stimulation can include deep brain stimulation (DBS), spinal cord stimulation (SCS), Occipital NS therapy, Trigemenal NS therapy, peripheral field stimulation therapy, sacral root stimulation therapy, or other such therapies. For example, DBS may include electrical stimulation of the thalamus or basal ganglia and may be used to treat disorders such as movement disorders such as essential tremor, Parkinson's disease (PD), and dystonia, and other physiological disorders. DBS may also be useful for traumatic brain injury and stroke. DBS may also be useful for treating depression, obesity, epilepsy, and obsessive-compulsive disorder, Tourette's Syndrome, schizophrenia, and other indications.

A stimulation procedure, such as DBS, typically involves first obtaining preoperative images, e.g., of the patient's brain, such as by using a computed tomography (CT) scanner device, a magnetic resonance imaging (MRI) device, or any other imaging modality. This sometimes involves first affixing to the patient's skull spherical or other fiducial markers that are visible on the images produced by the imaging modality. The fiducial markers help register the preoperative images to the actual physical position of the patient in the operating room during the later surgical procedure.

After the preoperative images are acquired by the imaging modality, they are then loaded onto an image-guided surgical (IGS) workstation, and, using the preoperative images displayed on the IGS workstation, a neurosurgeon can select a target region within the patient anatomy, e.g., within the brain, an entry point, e.g., on the patient's skull, and a desired trajectory between the entry point and the target region. The entry point and trajectory are typically carefully selected to avoid intersecting or otherwise damaging certain nearby critical structures or vasculature.

In the operating room, the physician marks the entry point on the patient's skull, drills a burr hole at that location, and affixes a trajectory guide device about the burr hole. The trajectory guide device includes a bore that can be aimed to obtain the desired trajectory to the target region. After aiming, the trajectory guide is locked to preserve the aimed trajectory toward the target region, and a microdrive introducer is then used to insert the surgical instrument along the trajectory toward the target region, e.g., of the brain. The surgical instrument may include, among other things, a recording electrode leadwire, for recording intrinsic electrical signals, e.g., of the brain; a stimulation electrode leadwire, for providing electrical energy to the target region, e.g., of the brain; or associated auxiliary guidewires or guide catheters for steering a primary instrument toward the target region, e.g., of the brain.

The stimulation electrode leadwire, which typically includes multiple closely-spaced electrically independent stimulation electrode contacts, is then introduced and positioned in close proximity to the tissue targeted for stimulation, to deliver the therapeutic stimulation to the target region, e.g., of the brain. An implanted pulse generator (IPG) generates electric pulses to transmit signals via the leadwire. The leadwire can include cylindrically symmetrical electrodes, which, when operational, produce approximately the same electric values in all positions at a same distance from the electrode in any plain that cuts through the electrode perpendicular to the central longitudinal axis of the leadwire. Alternatively, the leadwire can include directional electrodes that produce different electrical values depending on the direction from the electrode. The stimulation electrode leadwire is then immobilized, such as by using an instrument immobilization device located at the burr hole entry, e.g., in the patient's skull, in order for the DBS therapy to be subsequently performed.

The target anatomical region can include tissue that exhibit high electrical conductivity. For given stimulation parameter settings, a respective subset of the neural elements are responsively activated. A stimulation parameter can include, for example, a current amplitude or voltage amplitude, which may be the same for all of the electrodes of the leadwire, or which may vary between different electrodes of the leadwire. The applied amplitude setting results in a corresponding current in the surrounding neural elements, and therefore a corresponding voltage distribution in the surrounding tissue.

After the immobilization of the stimulation electrode leadwire, the actual stimulation therapy is often not initiated until after a time period of about two-weeks to one month has elapsed. This is due primarily to the acute reaction of the brain tissue to the introduced electrode leadwire (e.g., the formation of adjacent scar tissue), and stabilization of the patient's disease symptoms. At that time, a particular one or more of the stimulation electrode contacts is selected for delivering the therapeutic stimulation, and other stimulation parameters are adjusted to achieve an acceptable level of therapeutic benefit. The IPGs offer a wide range of stimulation settings which can be independently or concurrently varied in order to correspondingly alter the size, shape, and location of the volume of tissue being therapeutically affected by the stimulation.

Systems and methods are provided that facilitate exploration of target regions of stimulation and stimulation therapies to determine which therapy regimen is best suited for a particular patient or group of patients.

A treating physician typically would like to tailor the stimulation parameters (such as which one or more of the stimulating electrode contacts to use, the stimulation pulse amplitude, e.g., current or voltage depending on the stimulator being used, the stimulation pulse width, and/or the stimulation frequency) for a particular patient to improve the effectiveness of the therapy. Parameter selections for the stimulation can be achieved, for example, via trial-and-error. However, the use of guiding visualization software provides for efficient stimulation parameter selection. See Frankemolle, A. et al., "Reversing cognitive-motor impairments in Parkinson's disease patients using a computational modelling approach to deep brain stimulation programming," Brain 133 (3): 746-761 (2010). Indeed, systems and methods are provided that provide visual aids of the electrode location in the tissue medium along with computational models of the volume of tissue influenced by the stimulation, thereby facilitating parameter selection. See, for example, U.S. patent application Ser. No. 12/454,330, filed May 15, 2009, which published as U.S. Pat. App. Pub. No. 2009/0287271 ("the '330 application"), U.S. patent application Ser. No. 12/454,312, filed May 15, 2009, which issued as U.S. Pat. No. 8,326,433 ("the '312 application"), U.S. patent application Ser. No. 12/454,340, filed May 15, 2009, which published as U.S. Pat. App. Pub. No. 2009/0287272 ("the '340 application"), U.S. patent application Ser. No. 12/454,343, filed May 15, 2009, which published as U.S. Pat. App. Pub. No. 2009/0287273 ("the '343 application"), and U.S. patent application Ser. No. 12/454,314, filed May 15, 2009, which published as 2009/0287467 ("the '314 application"), the content of each of which is hereby incorporated herein by reference in its entirety. Those applications describe systems including equation-based models for generation of estimated volumes of activation (VOAs) based on input of stimulation parameters. The described systems and methods provide for estimation of stimulation volumes and display models of a patient anatomy and/or a stimulation leadwire, via which to graphically identify the estimated stimulation volumes and how they interact with various regions of the patient anatomy. If a physician selects a therapeutic stimulation parameter combination, the software displays a representation of the volume of surrounding tissue which is estimated to be activated by the system. See also S. Miocinovic et al., "Cicerone: stereotactic neurophysiological recording and deep brain stimulation electrode placement software system," Acta Neurochir. Suppl. 97(2): 561-567 (2007). FIG. 3 shows an example user interface, using which a user can input and/or modify stimulator settings in the left two panels, while the right panel shows a model of anatomical structures, an implanted leadwire, and an estimated VOA.

U.S. Prov. Pat. App. Ser. Nos. 61/521,583 ("the '583 application"), filed Aug. 9, 2011 and 61/690,270 ("the '270 application"), filed Jun. 22, 2012, and U.S. patent application Ser. No. 13/507,962, filed Aug. 9, 2012, which published as U.S. Pat. App. Pub. No. 2013/0116744 ("the '962 application"), each of which is hereby incorporated by reference in its entirety, further describe generation of a VOA on a fiber specific basis.

SUMMARY

According to an example embodiment of the present invention, a stimulation leadwire apparatus includes a plurality of leadwires connected to a programming source, e.g., an implanted pulse generator (IPG) including a plurality of ports to the leadwires, where the leadwires include a multitude of electrodes. In an example embodiment, the arrangement further includes multiplexers by which to select particular ones of the leadwires and electrodes. The electrodes, or at least a portion thereof, are controllable for emitting electrical pulses to stimulate an anatomical region, e.g., the brain, of a patient in whom the leadwire is implanted. Additionally, the electrodes, or at least a portion thereof, according to one example embodiment, are usable as sensors for sensing effects of the stimulation. Because of the inclusion of a multitude of leadwires and electrodes, the electrodes can be placed at many different locations with stimulations and sensing performed at the many locations, by which much information can be accumulated, based on which the system, according to an example embodiment, generates a patient-specific interaction model that associates stimulation sites and their corresponding stimulation parameters to affected neuromodulation sites. For example, the system controls the electrodes to perform a stimulation, obtains sensor readings from the electrodes, and modifies the stimulation parameters according to the sensor readings. The system uses sensor information obtained over a plurality of such applied stimulations to generate and/or update the patient-specific interaction model. Further, in an example embodiment, the system modifies the stimulation parameters based on the patient-specific interaction model which has been updated according to the sensor information indicating effects of the prior stimulations. However, as explained below, the patient-specific interaction model can alternatively or as a supplement be generated based on other input such as a tractography map.

Further, the present invention provides example methods that simplify parameter selection so that a system with a multitude of implanted electrodes positioned at a plurality of anatomical locations is not too unwieldy. For example, the system uses models by which a user can select a desired outcome at a neuromodulation effect region, and the system selects the particular electrodes to implement and the particular settings to use for those electrodes, so that the user need not select parameters for each of the multitude of electrodes. Thus, the mappings allow for implementation of such a system that includes a multitude of electrodes.

Example embodiments of the present invention provide a sensing and stimulation system that is configured to stimulate and sense at multiple sites of a neural system simultaneously. The system is configured for the stimulation to be performed either in an open-loop mode or a closed-loop mode in which the stimulation is in response to raw or processed sensed information. The system includes one or more modules for stimulating one or more anatomical regions, tissue, and/or structure. The one or more modules are configured to simultaneously sense in multiple sensing sites and stimulate one or more stimulation sites.

According to an example embodiment, the system is configured to obtain sensor information and/or user input for determining a state of the patient and/or a state of the system, and, based on such information in association with stimulation information, generate a transfer function, also referred to herein as a patient-specific interaction model, that associates stimulation sites and the associated stimulation parameters with affected neuromodulation sites.

For example, according to an example embodiment, the system stimulates a plurality of anatomical sites, one by one, at one stimulation parameter set or at multiple stimulation parameter sets. For each such stimulation, the system uses information obtained from sensors and/or from user input information regarding the effect of the respective stimulations on the patient, thereby learning a correlation of stimulation sites to affected neuromodulation sites, such correlation forming a patient-specific interaction model that predicts affected neuromodulation sites for particular stimulation sites (e.g., which can differ for different stimulation parameters). The system is configured to use the interaction model to thereafter output a suggested stimulation site (and stimulation parameters) in response to user input of one or more targeted neuromodulation regions. For example, based on the known transfer function, the system uses an optimization algorithm to determine the suggested one or more stimulation sites and one or more parameter sets for effecting the neuromodulation at the one or more target sites, which may be different than the stimulation sites. For example, according to one example embodiment, the system initially assumes a linear expandability of the interaction model to obtain initial candidates and then refines the candidate selection using any suitably appropriate optimization, e.g., a gradient descent optimization algorithm.

According to an example embodiment, the system is configured to stimulate one or more sites and sense (e.g., local field potentials (LFP), action potentials at individual neurons, mean firing rate, power at a particular frequency bands) either simultaneously or sequentially at multiple sites, and, according to an example embodiment, the system is configured to modify the stimulation at the one or more sites based on the sensing at the multiple sites. Epilepsy is one of the only indications where stimulation responsive to sensing has been shown to have value. In spinal cord stimulation (SCS), sensing has also been shown to have value (Saluda/NICTA) for managing the amplitude for a patient. Clinical evaluations are being performed, and the system according to the present invention can help perform evaluations, to determine further value in such sensing. Specifically, example embodiments provide for sensing at the multiple sites and/or using sensed action potentials, mean firing rate, and/or frequency band specific power, as mentioned, which provide an enhanced closed-loop operation.

In an example embodiment, the system further includes a module for visualizing (and/or outputting a listing of) areas and/or components of the neural system expected to be affected by stimulation at the one or more stimulation sites. The module is configured to determine the expected sites based on a system model (the model can be derived from patient-specific radiographic data, an atlas-like model, information derived from evoked responses to stimulation as measured by the system, information compiled from similar data into an average-patient model, or information derived from PET, MRI, or other functional imaging data).

The system, according to example embodiments, includes algorithms for automated determination of interaction models, and to automatically derive stimulation solutions to a user defined stimulation goal, e.g., stimulation of areas X and Y and inhibition of A and B to achieve a particular goal) (open-loop or closed-loop in response to an observed signature (e.g., LFP, mean firing rate, etc.)). Further in this regard, the use-input goal can be to produce certain neuromodulation effects and/or to reduce neural activity in one or more regions. For example, a sensor might sense neural activity in one or more regions which neural activity a clinician can input should be reduced. The system can then use an optimization algorithm to output at which one or more regions to perform a stimulation, and with which stimulation parameters, to most effectively achieve the indicated neuromodulation at the indicated sites and to most effectively reduce the indicated neural effects (e.g., at the indicated regions).

Further, the system is highly scalable, and therefore can be used to interact with complex multi-site neural systems (of which type most neural systems are), and for new and improved therapies in response to advancements in spatio-temporal interaction with the nervous system.

According to example embodiments of the present invention, a leadwire includes more than 16 electrodes and the system is configured to control stimulation using such a leadwire. According to an example embodiment, the system is scalable to provide, control, and monitor hundreds of electrodes.

According to an example embodiment, the system provides a neural system visualization aid, which can help a clinician adjust the complex stimulation program.

According to an example of the present invention, a computer-implemented method includes receiving, by a computer processor, user input selecting a neuromodulation effect region of a patient; and responsive to the input, determining, by the processor, electrode neuromodulation settings estimated by the processor to, when applied to an implanted electrode leadwire, produce a volume of tissue activation that at least partially encompasses at least one target anatomical stimulation candidate region which is mapped by the processor to, and is at a distance from, the selected neuromodulation effect region.

According to an example aspect of the method, the leadwire is implanted in the patient's brain. Alternatively or additionally, the at least one target anatomical stimulation candidate region includes a plurality of distinct regions. Alternatively or additionally, the user input specifies the neuromodulation effect region as the region at which neural activity is to be reduced. Alternatively or additionally, the mapping is based on a susceptibility weighted imaging (SWI) image. Alternatively or additionally, the mapping is based on a probabilistic tractography model. Alternatively or additionally, the mapping includes a patient-specific mapping that is specific to the patient and that is based on the response information indicating prior responses by the patient to previous neuromodulations.

According to an example aspect of the method, which can be provided in combination with any one or more of the above-noted aspects, the selected neuromodulation effect region is one of a plurality of neuromodulation effect regions selected by the user input, and the determining includes determining one or more sets of neuromodulation settings to be distributed to one or more electrodes of the leadwire to produce a selected therapeutic effect at the plurality of neuromodulation effect regions.

According to an example aspect of the method, which can be provided in combination with any one or more of the above-noted aspects, the mapping performed by the processor is performed by extrapolating new stimulation parameters from modeled stimulation parameters that are mapped in the model to neuromodulation effect regions, which stimulation parameters are estimated, by the processor and based on the model, to produce a selected effect at the selected neuromodulation effect region, the selected effect at the selected neuromodulation effect region not being mapped in the model.

According to an example aspect of the method, which can be provided in combination with any one or more of the above-noted aspects, the method further includes generating the mapping, and the generation of the mapping includes: performing a plurality of neuromodulations at a respective plurality of sets of neuromodulation settings; and recording, for each of at least a subset of the neuromodulations, at least one neuromodulation effect occurring at a respective one or more anatomical regions, the one or more anatomical region being responsively mapped by the processor to a respective one or more stimulation regions of tissue estimated by the processor to have been activated by the respective neuromodulation.

According to an example further aspect of the immediately preceding aspect, the mapping is the patient-specific mapping and the plurality of neuromodulations are performed on the patient.

According to an example further aspect of either of the two immediately preceding aspects, at least some of the neuromodulation effects are sensed by electrodes of the leadwire.

According to an example further aspect of the immediately preceding aspect, the plurality of neuromodulations are performed by electrodes of the leadwire different than the electrodes that sensed the at least some of the neuromodulation effects. Alternatively, each of at least a subset of the electrodes of the leadwire are configured to both perform a neuromodulation and sense an effect of a neuromodulation.

According to an example further aspect of any of the preceding aspects according to which neuromodulation effects are recorded, at least some of the neuromodulation effects are input by a user.

According to an example aspect of the method, which can be provided in combination with any one or more of the above-noted aspects, the leadwire includes more than 16 electrodes; the leadwire is controlled via an implanted pulse generator that is configured to cause 32 electrodes of the leadwire to simultaneously output an electrical stimulation pulse; and/or the leadwire is one of a plurality of leadwires that are all controlled via an implanted pulse generator that is configured to cause 32 electrodes of the plurality of leadwires to simultaneously output an electrical stimulation pulse.

According to an example aspect of the method, which can be provided in combination with any one or more of the above-noted aspects, the method further includes controlling electrodes of the implanted leadwire to perform a neuromodulation therapy according to the determined settings; obtaining sensor readings from the electrodes; and responsive to the sensor readings, modifying the stimulation settings.

According to an example further aspect of the immediately preceding aspect, the method further includes receiving over time a plurality of user input of clinical states; and correlating, by the processor, the user input clinical states to biopotential signatures sensed by electrodes at times to which the clinical states respectively correspond. Further, the sensor readings, responsive to which the settings are modified, indicate respective biopotential signatures, and the modification is based on the correlation.

According to an example further aspect of the aspect according to which the stimulation settings are modified responsive to the sensor readings, the sensor readings: indicate a mean firing rate of neural elements, the modification being based on the mean firing rate; are power readings at a specified frequency band; and/or are of local field potentials.

According to an example aspect of the method, which can be provided in combination with any one or more of the above-noted aspects, the leadwire is one of a plurality of leadwires, each of the leadwires including at least one respective electrode controlled by an implanted pulse generator (IPG), the IPG including a plurality of ports; and at least one multiplexer is provided between a respective one of the ports and a respective subset of more than one of the plurality of leadwires, which multiplexer is configured to select between the subset of the more than one of the plurality of leadwires for application to the electrodes thereof, of a signal from the respective port, the signal causing the electrodes thereof to produce electrical pulses for neuromodulation of tissue in which the subset of leadwires is implanted.

According to an example of the present invention, a computer-implemented method includes controlling electrodes of an implanted leadwire to perform a neuromodulation therapy according to a set of stimulation parameters; obtaining sensor readings from the electrodes; and responsive to the sensor readings, modifying the stimulation parameters.

According to an example aspect of the method, the method further includes receiving over time a plurality of user input of clinical states; and correlating, by the processor, the user input clinical states to biopotential signatures sensed by electrodes at times to which the clinical states respectively correspond. Further, the sensor readings, responsive to which the stimulation parameters are modified, indicate respective biopotential signatures, and the modification is based on the correlation.

According to an example aspect of the method, which can be provided in combination with the preceding aspect, the method further includes receiving user input of a plurality of states, and, for each of the plurality of states, a respective set of stimulation parameters to be applied responsive to sensing of the respective state, where at least one of the states is defined according to a reading of a non-implanted sensor; time-correlating, by the processor, readings of the electrodes of the leadwire to readings of the non-implanted sensor; and substituting, by the processor, the definition of the at least one of the states with an alternate definition of a state according to a reading of the electrodes of the leadwire; where the modifying is performed based on the alternate definition.

According to an example aspect of the method, which can be provided in combination with any one or more of the above-noted aspects of the method, the modification is based on sensor readings of a plurality of the electrodes positioned at a respective plurality of anatomical locations.

According to an example aspect of the method, which can be provided in combination with any one or more of the above-noted aspects of the method, the sensor readings indicate a mean firing rate of neural elements, the modification being based on the mean firing rate.

According to an example aspect of the method, which can be provided in combination with any one or more of the above-noted aspects of the method, the sensor readings include power readings at a specified frequency band.

According to an example aspect of the method, which can be provided in combination with any one or more of the above-noted aspects of the method, the sensor readings include readings of local field potentials.

According to an example embodiment of the present invention, a stimulation system includes an implanted pulse generator (IPG) including a plurality of ports; a plurality of leadwires, each of the leadwires including at least one respective electrode; and at least one multiplexer between a respective one of the ports and a respective subset of more than one of the plurality of leadwires, which multiplexer is configured to select between the subset of the more than one of the plurality of leadwires for application to the electrodes thereof, of a signal from the respective port, the signal causing the electrodes thereof to produce electrical pulses for neuromodulation of tissue in which the subset of leadwires is implanted.

The various components and methods described herein may be practiced and/or provided, each alone, or in various combinations.

An example embodiment of the present invention is directed to a processor, which can be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. The memory device can include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to a hardware computer-readable medium, e.g., as described above, having stored thereon instructions executable by a processor to perform the methods described herein.

An example embodiment of the present invention is directed to a method, e.g., of a hardware component or machine, of transmitting instructions executable by a processor to perform the methods described herein.

DETAILED DESCRIPTION

Figure 1:
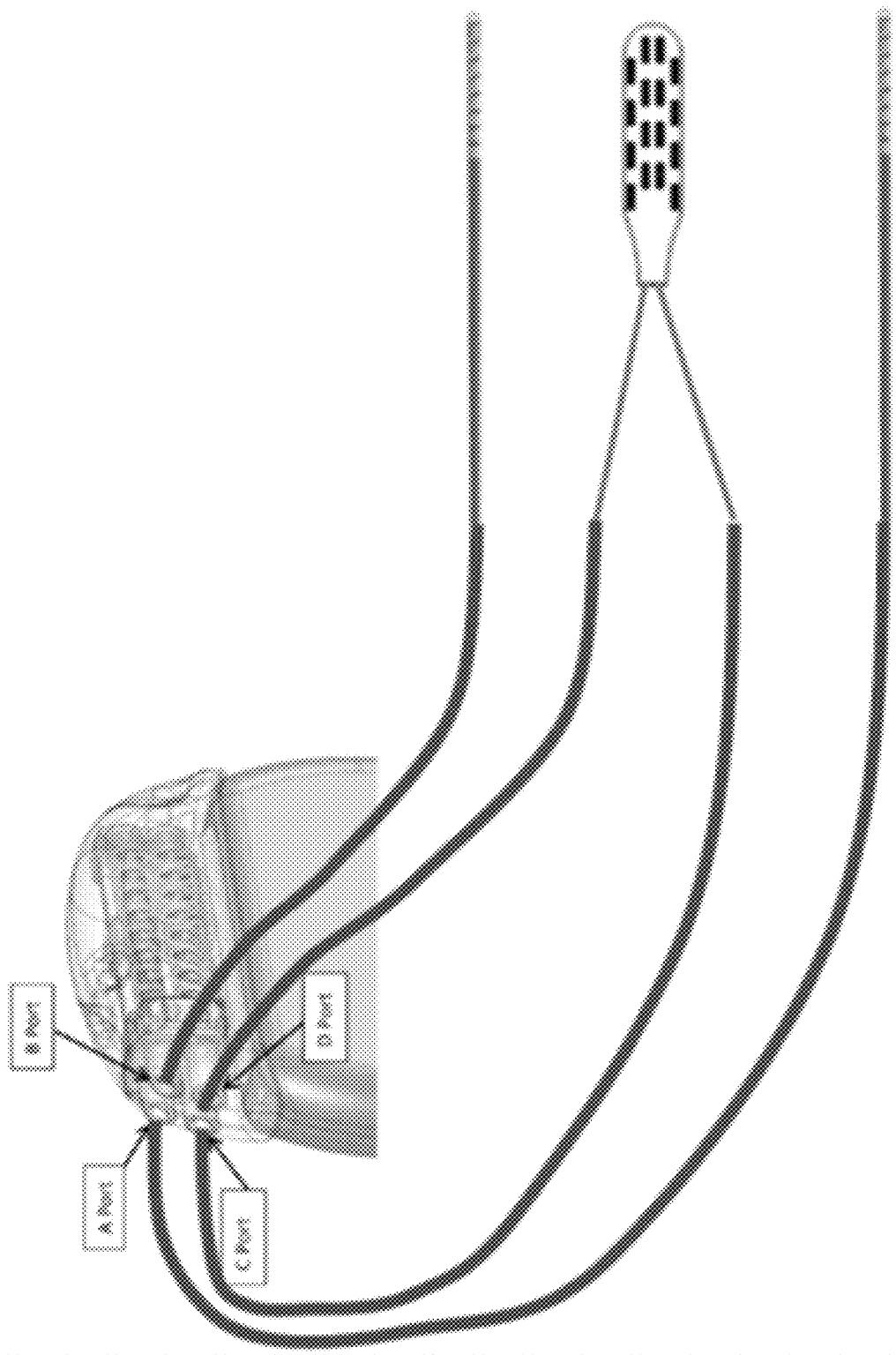
FIG. 1 illustrates a sensing and stimulation device, according to an example embodiment of the present invention.

According to an example embodiment, a system includes at least one active stimulation/sensing module with a power source.

According to an example embodiment, the system includes more than one module, providing scalability. A plurality of the modules can be powered by a primary module or each can have its own power source. In an example embodiment, the multiple modules are interconnected by wires (or another tangible connection). Alternatively, the modules are wirelessly connected. Still further, according to an example embodiment, the system includes both wired and wireless connections between the modules.

According to an example embodiment, the system includes and manages stimulation and sensing of one or more leadwires that include more than 16 sensing/recording electrodes. A multiple current sources architecture (as opposed to a single voltage or current source for all of the electrodes) is the optimal stimulation architecture because it provides the best opportunity for stable stimulation, and enables fine tuning of stimulation at one or more stimulation sites.

According to example embodiments of the present invention, the system is configured to record at multiple locations simultaneously (or nearly simultaneously via high sampling rates) and stimulate at least one site. Sensed data from the multiple sites can be processed together to drive stimulation at the one or more sites.

Thus, for example, according to an example of the present invention, a method includes controlling electrodes of an implanted leadwire to perform a neuromodulation therapy according to a set of stimulation parameters; obtaining sensor readings from the electrodes; and responsive to the sensor readings, modifying the stimulation parameters. Further, according to an example, the modification is based on sensor readings of a plurality of the electrodes positioned at a respective plurality of anatomical locations. Below, a leadwire system particularly suitable for use to perform the sensing and stimulating is described, where the system includes electrodes positioned at many anatomical locations for sensing and/or stimulating.

The system also supports stimulation programmed in an open-loop mode. The system also supports sensing in an open-loop mode, where the system provides the user with sensed data (raw or processed) via a user interface, which data can help the user know if an electrode is in the right location (e.g., via knowledge of evoked potential signatures), and otherwise help the clinician/physician interact with the neural system. Note that the stimulation response can be programmed to occur in one or multiple places that can, but need not, coincide with the sensing site(s).

The utility of a system with such complexity is greatly enhanced by visualization and algorithms. Thus, according to example embodiments of the present invention, the system provides visualization components which help the physician to estimate how stimulation at one site affects other sites. According to an example embodiment, the system performs an estimation of stimulation effect (which it visualizes) based on patient-specific data, such as a probabilistic tractography model based on a diffusion tensor imaging (DTI) or susceptibility weighted imaging (SWI) image. According to an example embodiment, the tractography model is combined with a computational model of stimulation so that the effect of stimulation parameters (e.g., pulse width (PW), amplitude, rate, field configuration in terms of, e.g., anode/cathode and percentages) is included in the visualized estimate. In other words, a computation stimulation model is used to determine an electric field, activation thresholds, and therefore an immediate estimated activation region, and then the tractography model is applied to the computation stimulation model to determine which neural elements are in the immediate estimated activation region, the system following the extension of such neural elements to determine outlying sites which would be affected by those neural elements. In an example embodiment, the computational model includes linear (e.g., a simple model that fits definition of linear systems) or non-linear (e.g., including a differential equation and a solution thereof) models of representative neural elements.

According to an example embodiment, in instances where a patient-specific tractography data set is not available, the system is configured to register another tractography model or atlas (e.g., a patient population model or atlas that is registered to the patient) to create the estimate for a given patient. Other radiographic elements can be used to contribute to the interaction model (e.g., functional imaging such as fMRI, PET, EEG, MEG, etc.). For example, according to an example embodiment, the system generates a tractography model based on MR imaging.

In an example embodiment, the system allows the user to select points in the brain where neuromodulation is desired, and executes an algorithm that identifies candidate stimulation sites that are likely to affect one or more of the brain areas that the user desires to neuromodulate. In an example embodiment, the system produces an output for the candidate sites to be visualized by the user, and uses different colors (or other visual properties) to identify locations connected to a given brain area that the user has identified as a neuromodulation target. One advantage of the tool is that locations can be identified that are likely to enable neuromodulation of multiple candidate targets, i.e., "nodes" that represent candidate surgical and stimulation targets for achieving the input goals, which can include neuromodulation targets and/or sites at which certain neural activity is to be inhibited. These tools are likely to be helpful preoperatively, when the clinician is working to identify stimulation targets for a specific patient.

Thus, according to an example, a method includes receiving, by a computer processor, user input selecting a neuromodulation effect region of a patient; and responsive to the input, determining, by the processor, electrode neuromodulation settings estimated by the processor to, when applied to an implanted electrode leadwire, produce a volume of tissue activation that at least partially encompasses at least one target anatomical stimulation candidate region which is mapped by the processor to, and is at a distance from, the selected neuromodulation effect region. In an example, the user-selected points can be at a plurality of distinct regions, which the processor determines would be affected by one or more direct stimulation sites.

As mentioned above, the mapping between the user-selected region(s) and the stimulation candidate region(s) can be based on a SWI image and/or a probabilistic tractography model.

Further, according to an example embodiment, the mapping can be based on response information indicating prior responses by the patient to previous neuromodulations. For example, according to an example embodiment of the present invention, the system includes sensors for sensing patient responses to stimulation, and the system is configured to create a patient-specific neural site interaction model of expected activation and inhibition based on the sensed information. For example, the system uses a stimulation paradigm (which can include various parameters, waveforms, and/or temporal patterns) to perform a stimulation and evaluates a response to the stimulation using some characteristic, e.g., the power in a certain part of the spectra of the recorded signal. (The paradigm used can be manually selected or can be preprogrammed into the system based on an understanding of best practices.) The evaluated paradigm can include multi-site stimulation. Thus, example embodiments provide a system that generates a patient-specific response model based on biopotential responses to stimulation, tractography, fMRI, PET, source-localization (i.e., using recordings, estimating sources that caused sensed signals), and/or other data.

In an example embodiment, the system includes an automated algorithm for stimulating a defined set of sites, one at a time (and, according to an example embodiment, repeatedly with different parameters), e.g., using current steering (see, e.g., U.S. Prov. Pat. App. Ser. No. 61/753,232, filed Jan. 16, 2013 and U.S. patent application Ser. No. 14/011,870, filed Aug. 28, 2013, which published as U.S. Pat. App. Pub. No. 2014/0066999, the entire contents of each of which is hereby incorporated by reference in its entirety), and sensing the evoked responses to the stimulation at one or more of the defined set of sites, to create an interaction model specific to that patient. The automated algorithm, causing the processor to trigger the pulses for the stimulation, can be executed under the watchful eye of a clinician, and can include causing brief stimulations where response latencies permit.

The sensed responses, and therefore the sensing, can be at sites other than those being stimulated. In other words, stimulation at location A can cause a response at location B. According to an example embodiment, the algorithm includes automated evaluation of simultaneous multi-site stimulation and sensing at one or more sites, to expand the interaction model. The number of multi-site stimulation combinations may be large, and automatic testing of all of the possible combinations can be inefficient. Therefore, according to an example embodiment, the system gives the user the capability to choose specific types of stimulation (e.g., only anodic monopolar stimulation, only cathodic monopolar stimulation, with particular pulse widths, certain specified frequencies of pulses, etc.) to include for the algorithmic automated evaluation, and is also given the capability to manually prescribe specific stimulation configurations to test and add to the neural system interaction model.

According to an example embodiment, the system provides an "inverse" capability, whereby the system obtains user-input of an identification of a desired system-level response to stimulation (e.g., excite one or more neural areas, and/or inhibit one or more neural areas), and the system executes an algorithm to do one or more of the following: (1) evaluate stimulation paradigms (via evoked responses sensed by the system), search the stimulation parameter space (stimulation sites, parameters such as PW, rate, amplitude, configuration, and spatio-temporal stimulation paradigms between sites) for a stimulation paradigm that achieves the user-described stimulation objective, and output the determined paradigm with stimulation parameters to the user, i.e., the system iteratively tries new paradigms and parameters until the system achieves or gets close to the input goal, which can be determined based on sensor and/or user input data; (2) use the interaction model (radiographically-derived and/or evoked potential-derived, as described above) and determine and provide to the user a stimulation paradigm (could be single-site or multi-site with independent stimulation parameters for each site, and the spatio-temporal relationship of stimulation, i.e., when to stimulate where, may be part of the paradigm), i.e., use the interaction model to estimate which stimulation sites and settings would result in the desired goal; and (3) provide information, such as a visualization of the stimulation to response mapping, the interaction matrix, etc., to the user for evaluating the paradigms and searching for stimulation parameters. Note that for parameter spaces that are particularly vast, and/or for systems that are nonlinear, genetic optimization algorithms and/or support vector machine-based algorithms are good candidates for use for selecting a stimulation paradigm and associated parameters.

Thus, according to an example, the processor generates the model by performing a plurality of neuromodulations at a respective plurality of sets of neuromodulation settings; and recording, for each of at least a subset of the neuromodulations, at least one neuromodulation effect occurring at a respective one or more anatomical regions, the one or more anatomical region being responsively mapped by the processor to a respective one or more stimulation regions of tissue estimated by the processor to have been activated by the respective neuromodulation. However, in an example, the mapping performed by the processor between a target anatomical stimulation candidate region and user-selected neuromodulation effect region is performed by extrapolating new stimulation parameters from modeled stimulation parameters that are mapped in the model to neuromodulation effect regions, which stimulation parameters are estimated, by the processor and based on the model, to produce a selected effect at the selected neuromodulation effect region, and the selected effect at the selected neuromodulation effect region need not be mapped in the model itself.

Figure 6:
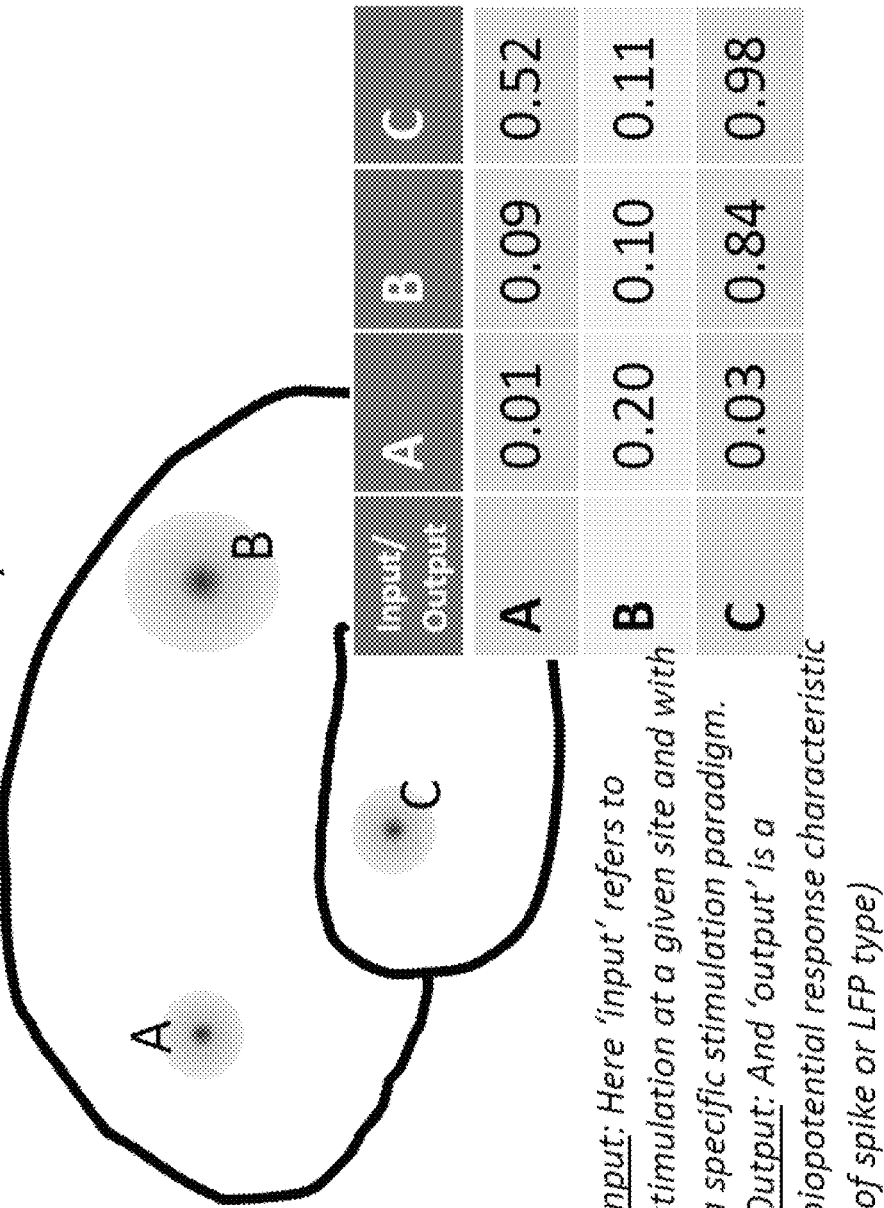
FIG. 6 shows a probabilistic patient-specific biopotential-based model showing an expected neuromodulation effect at sites A-C (columns in the illustrated chart) for stimulations at respective ones of the sites A-C (rows in the illustrated chart), according to an example embodiment of the present invention.
Figure 7:
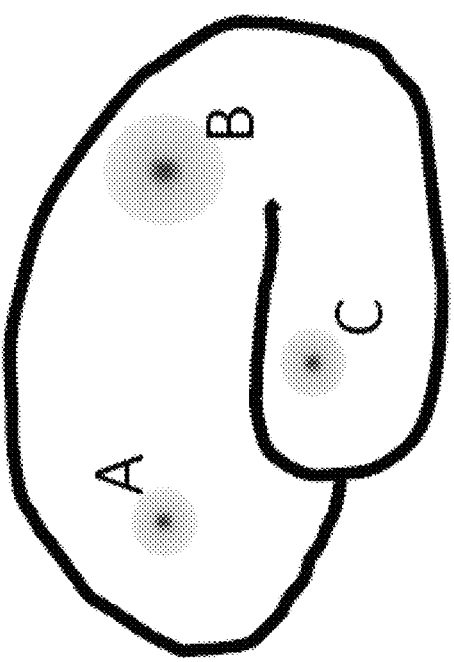
FIG. 7 shows an example user interface display that graphically identifies areas likely to be affected by a particular stimulation paradigm, according to an example embodiment of the present invention.

For example, FIG. 6 shows an example patient-specific interaction model, where the rows represent the stimulation sites and the columns represent the resulting neuromodulation effect at various sites. For example, row A shows that a stimulation at a particular parameter set at site A produces a change in a particular neuromodulation effect (e.g., local field potential (LFP), power at a particular frequency band, and/or neuro-activation spike) at each of sites A, B, and C, where the change is minimal at sites A and B (0.01 and 0.09, respectively) but larger at site C (0.52). Rows B and C similarly show changes occurring at sites A-C in response to stimulations at sites B and C, respectively.

In an example embodiment, the system initially applies assumptions of linearity of those relationships with respect to stimulation parameters (an increase in stimulation amplitude, for example, is assumed to cause a linear increase in the indicated changes) and/or with respect to combinations (stimulation at sites A and B assumed to produce an additive effect of the stimulations at sites A and B individually). After obtaining candidate stimulation sites and parameters based on the model with the linearity assumptions, the system applied a suitably appropriate optimization algorithm, e.g., a conventionally known gradient descent optimization routine or variation thereof, to further refine the suggested site(s) and parameter(s) to be used for achieving the target neuromodulation.

Figure 8:
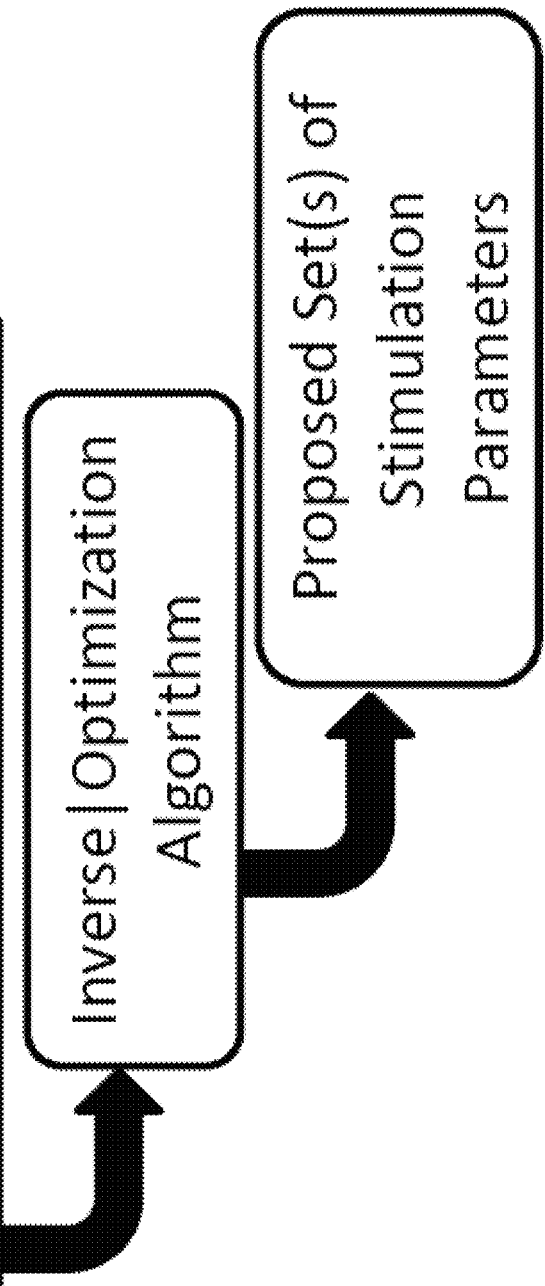
FIG. 8 shows an example data flow for the system to propose a stimulation paradigm and associated parameters in response to user input, according to an example embodiment of the present invention.

FIG. 8 shows a data flow of a method for outputting suggested stimulation sites and/or parameters for input target neuromodulation sites. FIG. 8 shows that a user defines a stimulation objective, e.g., to increase and/or reduce neural activity in one or more respective regions. In the example shown in FIG. 8, the user inputs a target of a modest increase in a particular defined characteristic (there can be any number of characteristics, such as LFP or spikes) at site A, no change at site B, and a robust inhibitory change at site C. The system then responsively performs an inverse optimization algorithm, as described, to determine suggested stimulation sites and/or parameters to achieve the input target neuromodulation effect at the indicated target sites, and then outputs the determined sites and/or parameters as a suggestion to the user.

It is noted that the patient-specific interaction model (alone or in combination with the optimization algorithm) can indicate multiple ways by which to produce the targeted neuromodulation, but it can occur that one way involves stimulation at more sites than another way, in which case, according to an example embodiment, the system takes this into consideration when suggesting a stimulation paradigm, stimulation at fewer sites being considered more optimal all else being equal.

According to an example embodiment, the development of interaction models and the determination of the solution to the "inverse" problem are automated so that the physician/clinician/user would only define the system-level stimulation goal, and the system would automatically determine and output to the user a desired stimulation paradigm (which may be very complex).

In an example embodiment of the present invention, the system outputs a user interface display that shows the user which parts of the neural system likely are able to be affected (an ability-to-impact model), for example, based on the interaction models. Such output can give the user a sense of constraints when defining the stimulation goal (for a given implanted system). When the interaction model is non-invasively derived, e.g., via tractography, functional imaging, etc., this output can be helpful for surgical planning, where the ability-to-impact model is specific to candidate electrode sites. For example, the system can output the ability-to-impact model for each of a plurality of leadwire sites input by the user, and provide the ability-to-impact model for each of the input leadwire sites. The user can then select whichever site provides the best possible coverage.

According to an example embodiment, the user can define a stimulation goal and set the system to run in an open-loop mode. The user can also alternatively set a stimulation goal to dynamically change responsive to a sensed system state. For example, the user can define one or more sensed system states, and one or more respective neural system stimulation goals (with corresponding stimulation paradigms), and define which stimulation paradigm is triggered for a given sensed system state.

The system provides tools for the user to define a sensed system state. The state can be defined by feedback parameters including, for example, sensor data (e.g., of external sensors wirelessly connected to the system) and/or user feedback (e.g., patient feedback input via a remote control). For example, according to an example embodiment, the power or changes in power in parts or all of the measured frequency spectrum at specific sites (e.g., the beta power in area A is high, and the gamma power in area D is also high) is one way of defining a sensed system state. Additionally or alternatively, the user can set the system to perform time-domain analyses for obtaining a system state on which basis to dynamically change the stimulation goal. Such analyses can include, for example, wavelet analysis, statistical measures, properties of single-unit firing patterns, i.e., firing patterns of action potentials of a single neuron, (e.g., inter-spike-interval relationships, i.e., the time between action potential and the patterns of such intervals, and/or other relationships concerning a neuron measureable with small electrodes).

A non-exhaustive list of example sensors used for system operation (based on the raw or processed data from the sensors) includes bio-potential sensor, chemical (e.g., neurotransmitter) sensors, temperature sensors, and physical sensors such as accelerometers, goniometers, etc. that may or may not be implanted. For example, in an example embodiment one or more external sensors are connected to the system wirelessly. In some embodiments, data sensed by these sensors contributes to (or comprises) the system interaction model on which basis the user can define stimulation goals (as described above). In some embodiments, the data sensed by these sensors alternatively or additionally provides a sensed system state, for example, for the closed-loop control.

Thus, for example, according to an example, a method includes a system controlling electrodes of an implanted leadwire to perform a neuromodulation therapy according to a set of stimulation parameters, obtaining sensor readings from the electrodes indicating a patient state, and, responsive to the state indicated by the sensor readings and based on the user-input state information, modifying the stimulation parameters.

Further, according to an example, the system receives over time a plurality of user input of clinical states and correlates the user input clinical states to biopotential signatures sensed by electrodes at times to which the clinical states respectively correspond, where the sensor readings responsive to which the stimulation parameters are modified indicate respective biopotential signatures, and the modification is based on the correlation.

In an example embodiment of the invention, data from non-implanted sensors (e.g., a blood pressure sensor) are time-correlated to data from implanted sensors using an algorithm (e.g., a support vector machine or artificial neural network), such that the user can define the sensed system state via external sensors, and a surrogate sensed system state based on sensing done by the implantable sensors can be defined (e.g., automatically) and used in the absence of external sensing tools. For example, the signal from external sensors is correlated to a measurement by the implanted system, and if there is good correlation, then the signal measured by the implanted system can be used instead. Thereafter, the sensed measurement from the electrodes of the implanted leadwire can be used for the closed-loop control.

Some example sensor readings which can be correlated by the system with states on which basis to modify the settings include mean firing rate, power readings at a specified frequency band, and local field potentials.

In an example embodiment, the system is configured to provide an interface via which a patient can define a state of being (e.g., a pain score, or a depression score, or a stress/anxiety score) at several points in time, and the system searches via algorithms for a sensed system state via the implantable sensors that correlates with the patient scores. That is, the system looks for signatures in the sensed data (e.g., biopotentials, such as voltages generated by biological systems, e.g., LFPs and action potentials) that correlate with the patient input about the patient's state. The sensor data and/or patient input can be provided in one or more sessions where an algorithm collects "training" data by which the biopotential signature-to-state relationships are determined. In an example embodiment, the algorithm is a dynamic learning algorithm that continuously updates as new "training" data is obtained via patient feedback (these algorithms can be particularly useful given the possibility and perhaps likelihood of plastic change in the neural system over time). Stimulation can then be set to be responsive to the sensed system bipotential state. Thus, based on the training data, the system associates biopotentials with particular patient states, and thereafter, the system can change which stimulation paradigms and/or stimulation settings in response to the biopotential state. Automated algorithms for defining the sensed system state are particularly useful because they, as noted above, make a system of such vast complexity usable in clinical practice.

For example, the system is configured to obtain from a patient and overtime, for each of a plurality of stimulation sessions, feedback, e.g., OK, Mild, Medium, Severe, etc., regarding particular symptoms, e.g., depression, stress, pain, etc., and, based on such feedback, update the preferred stimulation paradigm and parameters. Moreover, the feedback can be associated with biopotentials, which biotential signatures can serve as system states with which different stimulation paradigms are associated, so that the system changes which paradigm and settings are used at different sensed biopotentials. In an example embodiment, the system is configured to automatically stimulate using the updated preferred stimulation paradigm and parameters as long as the preferred program is within user-defined parameter constraints.

In an example embodiment, the system uses multiple independent current control (i.e., multiple current sources), thereby providing for a more stable stimulation, and a more fine-tuned stimulation (enables "virtual contacts" so that many stimulation sites can be defined with a fewer numbers of electrodes). The "virtual contacts" also enable higher resolution mapping of the neural system by centering stimulation at positions of the leadwire at which an electrode does not exist.

As described above, according to an example, the present system uses a patient-specific interaction biopotential analytics-based model or tractographical model to output a suggested stimulation paradigm for an input neuromodulation target. This significantly simplifies the setting by the clinician of stimulation parameters so that, according to example embodiments, the system can include one or more leadwires with numerous electrodes, e.g., 32 or more electrodes, even as many as into the hundreds of electrodes, since it is not required for the clinician to select which of the electrodes to use or the parameters to be used without any guidance on the stimulation regions on which to focus. Instead, the system can generate the patient-specific interaction model for a system including many electrodes. The user can input the target neuromodulation sites and effects, and, based on the model, the system outputs suggested combination of electrodes (at respective stimulation sites) and the respective simulation parameters for effecting the target neuromodulation response. (It is noted that the suggested stimulation paradigm can include a sequence of stimulations using different combinations of electrodes at different settings at different points throughout the sequence.)

Accordingly, FIG. 1 shows components of a system according to an example embodiment of the present invention, including an IPG with four ports A-D, each of which is shown with a wired connection to a respective set of 8 contacts. The respective eight contacts to which ports A and B are connected are on respective percutaneous cylindrical leads that are implanted, e.g., into the brain. The two sets of eight contacts to which ports C and D are connected are shown to be on a single paddle lead, i.e., the paddle lead includes 16 electrodes to which the IPG is connected via ports C and D. The paddle lead can be, according to an example embodiment, adapted for implantation on top of the brain.

Figure 2:
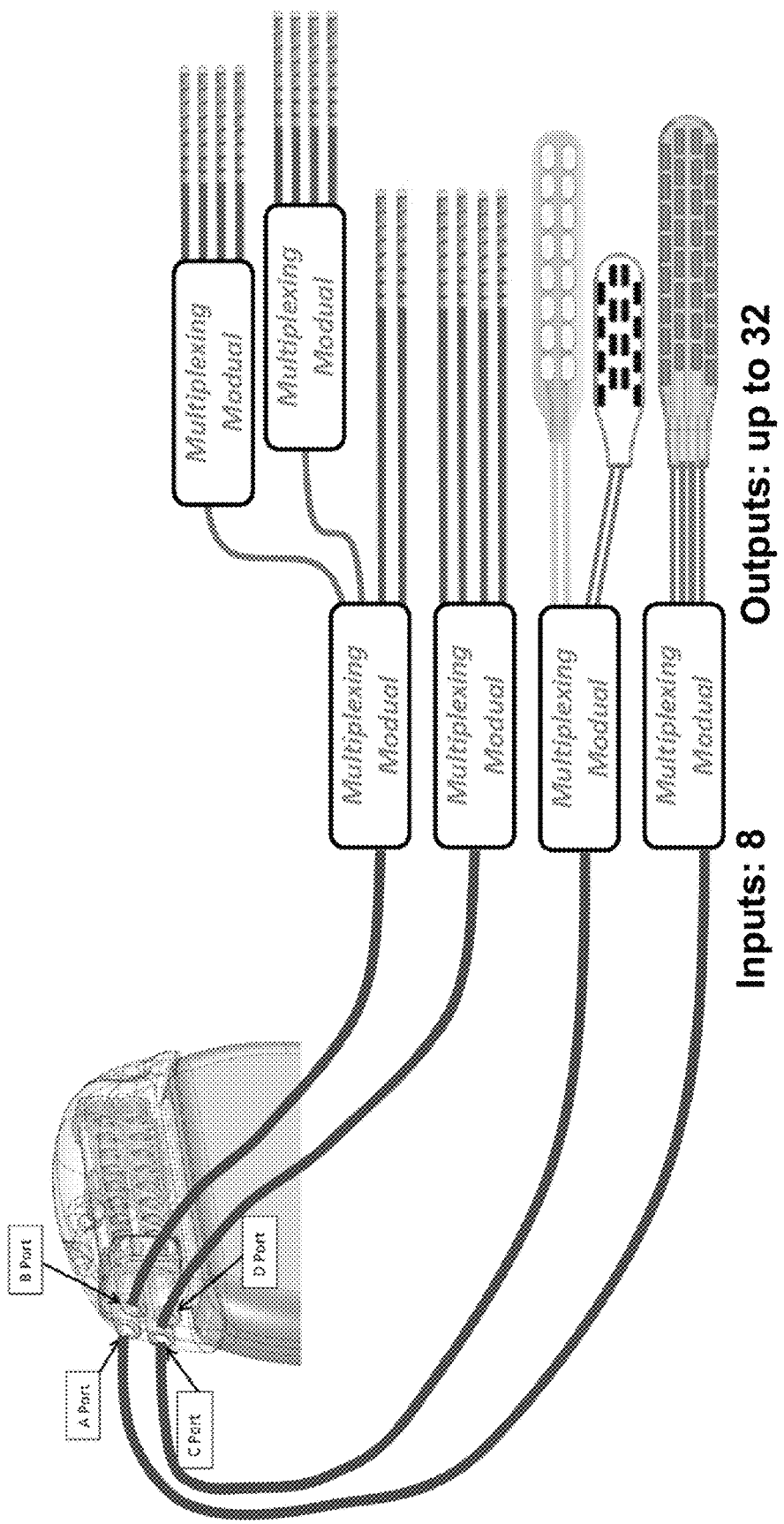
FIG. 2 illustrates a sensing and stimulation device with multiplexing modules, according to an example embodiment of the present invention.
Figure 3:
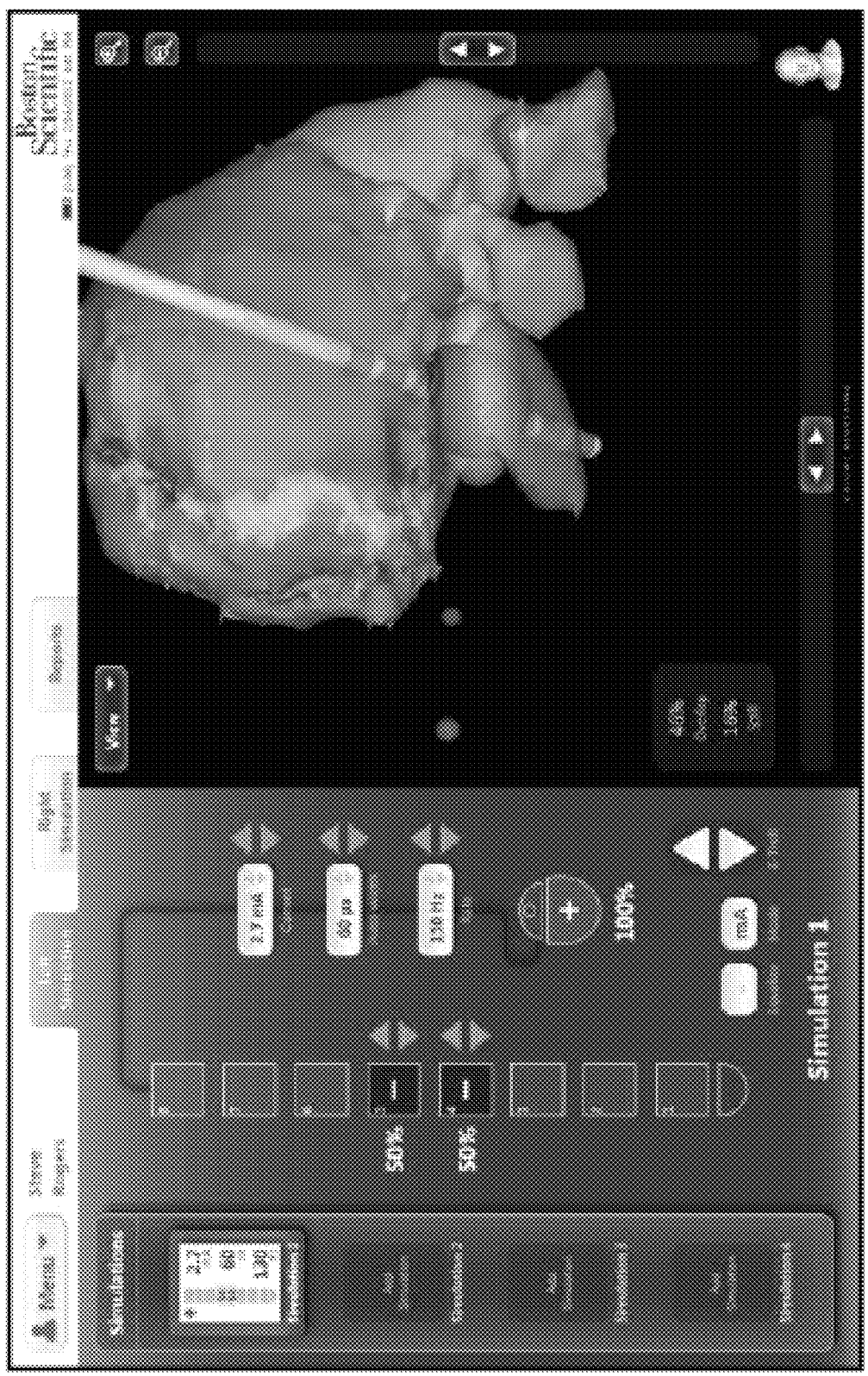
FIG. 3 is a conventional user interface for setting and visualizing stimulation programs.

FIG. 2 shows another example embodiment including 22 leadwires with a total of 176 electrodes, where the IPG is adapted for controlling 32 of the electrodes at any one time. The illustrated IPG includes four ports A-D each providing 8 inputs to a respective multiplexing module. Each of the multiplexing modules selects which of up to 8 electrodes, of a plurality of electrodes to which the respective multiplexing module is connected, to control based on the input from the IPG. This embodiment assumes that the system would select between various combinations of the 176 electrodes for achieving a target, where any output paradigm would include stimulation using, at any one time, only up to 32 electrodes. The paradigm can, however, include a sequence where different combinations of up to 32 electrodes from the 176 electrodes are used at different times, the paradigm potentially making use of all 176 electrodes. Additionally, these numbers are provided by way of example. Other embodiments may include a different number of total electrodes and may allow for a different number of the electrodes to be used simultaneously, e.g., more than 32.

Thus, according to an example embodiment of the present invention, a stimulation system includes an implanted pulse generator (IPG) including a plurality of ports; a plurality of leadwires, each of the leadwires including at least one respective electrode; and at least one multiplexer between a respective one of the ports and a respective subset of more than one of the plurality of leadwires, which multiplexer is configured to select between the subset of the more than one of the plurality of leadwires for application to the electrodes thereof, of a signal from the respective port, the signal causing the electrodes thereof to produce electrical pulses for neuromodulation of tissue in which the subset of leadwires is implanted.

Figure 4:
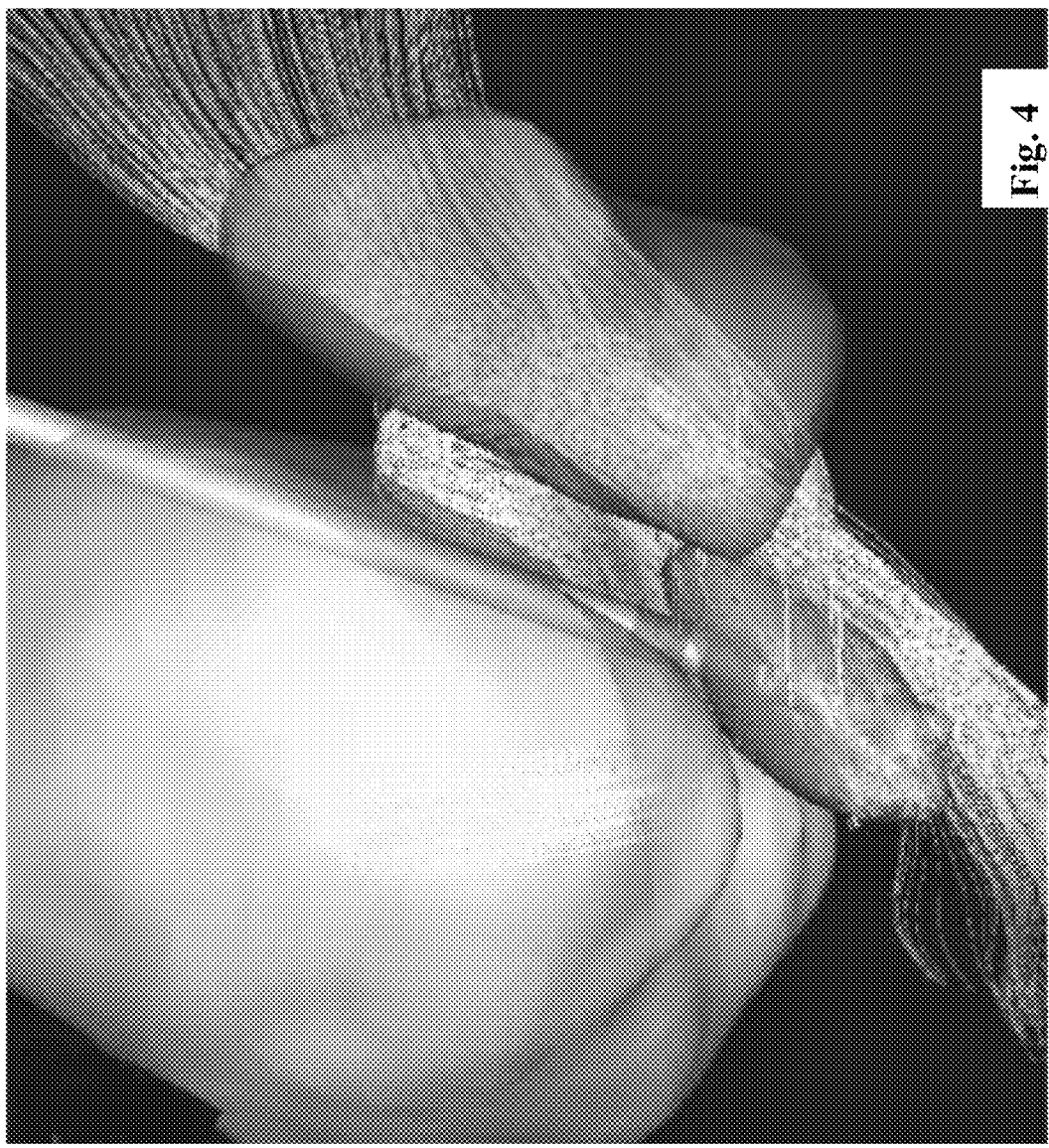
FIG. 4 shows an example display of a user interface showing a tractographical map and stimulation model according to an example embodiment of the present invention, where, although not shown in the grayscale image, different displayed neural element are displayed in different colors, where the different colors represent a corresponding neuromodulation effect.
Figure 5:
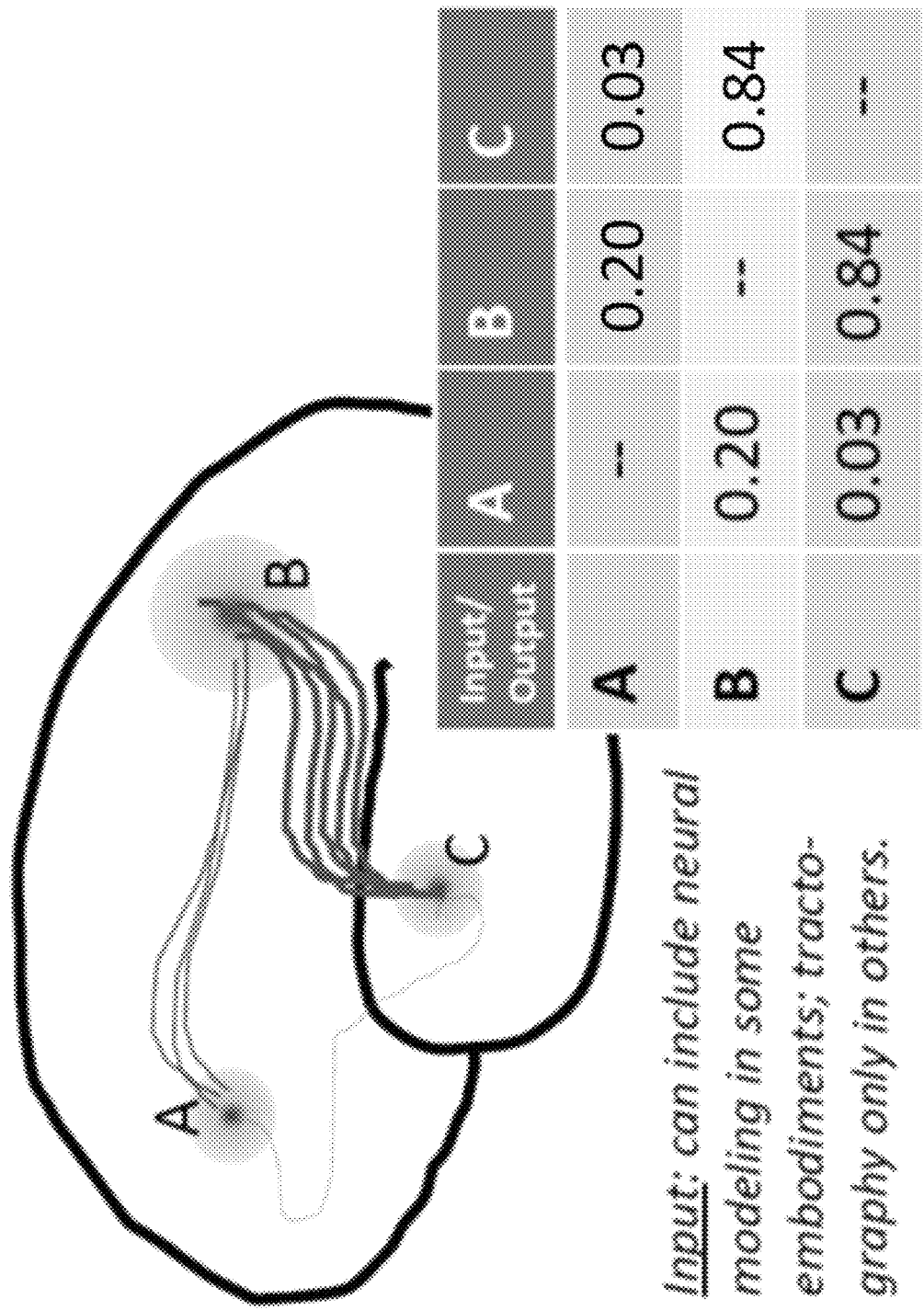
FIG. 5 shows a probabilistic patient-specific tractography-based model showing an expected neuromodulation effect at sites A-C (columns in the illustrated chart) for stimulations at respective ones of the sites A-C (rows in the illustrated chart), according to an example embodiment of the present invention.

FIG. 4 shows information captured in a tractography map, which can be used to understand relationships between different parts of brain by analyzing fiber paths from the image, as discussed above. FIG. 5 shows an example probabilistic tractographically based stimulation to neuromodulation mapping. For example, in an example embodiment, based on a tractography map, such as that shown in FIG. 4, the system determines that a stimulation at one region is expected to cause a neuromodulation response at another region (and vice versa) because of the extension of a neural element between those two regions. As described above, a probabilistic tractographic interaction model can be used instead of a biopotential response based model.

In an example embodiment, the probabilistic tractographical neuro modulation response mapping is based on a tractography map, such as one shown in FIG. 4, alone. In an alternative example embodiment, the probabilistic tractographical neuro modulation response mapping is additionally based on neural modeling including a model of a produced electric field in a patient anatomy at particular stimulation parameters and where such an electric field reaches a threshold for causing a neural activation. Combining such a neural model with a tractography map provides further refined data. Specifically, according to an example embodiment, the system uses the neural model to determine which neural elements would be activated at a particular stimulation paradigm, and then uses the tractography map to determine the neuromodulation sites that would be affected by those activated neural elements. For example, if the system determines from the neural model that site A would be activated, and determines that a particular neural element located at site A extends to site B, the system would estimate that site B would also be activated.

The above description is intended to be illustrative, and not restrictive. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the following claims.

What is claimed is:

1. A computer-implemented method comprising:
   receiving, by a processor and for each of a plurality of candidate stimulation sites, an indication of an indirect neuromodulation response for direct stimulation at each other of the candidate stimulation sites, wherein each of the candidate stimulation sites represents a portion of a brain that is distant from each other of the candidate stimulation sites;
   receiving, by a processor, a user-input of a desired stimulation response;
   determining, by the processor using the indications of the indirect neuromodulation responses for the candidate stimulation sites, at least one of the candidate stimulation sites for implantation of at least one electrode leadwire to stimulate the determined at least one of the candidate stimulation sites;
   determining or receiving, by the processor, electrode neuromodulation settings for performing neuromodulation on the brain of a patient using the at least one electrode leadwire implanted at the determined at least one of the candidate stimulation sites; and
   communicating the electrode neuromodulation settings for reception by an implantable pulse generator to perform neuromodulation in the brain of the patient using the at least one electrode leadwire coupled to the implantable pulse generator.

2. The method of claim 1, wherein the indication of the indirect neuromodulation responses for the candidate stimulation sites is a change in a local field potential, an action potential of at least one neuron, a mean neuron firing rate, a change in power at a particular frequency band, or a neuroactivation spike.

3. The method of claim 1, wherein receiving the indication of the indirect neuromodulation responses for the candidate stimulation sites comprises measuring the indication using at least one sensor.

4. The method of claim 3, wherein the at least one sensor is a bio-potential sensor, a chemical sensor, a temperature sensor, an accelerometer, or a goniometer.

5. The method of claim 1, wherein receiving the indication of the indirect neuromodulation responses for the candidate stimulation sites comprises estimating the indirect neuromodulation response at the candidate stimulation site using a probabilistic tractography model or a biopotential response model.

6. The method of claim 5, wherein estimating the indirect neuromodulation response comprises estimating the indirect neuromodulation response at the candidate stimulation site using the probabilistic tractography model, wherein the probabilistic tractography model is based on diffusing tensor imaging or susceptibility weighted imaging.

7. The method of claim 5, wherein estimating the indirect neuromodulation response comprises estimating the indirect neuromodulation response at the candidate stimulation site using the probabilistic tractography model, wherein the probabilistic tractography model is based on functional magnetic resonance imaging.

8. The method of claim 1, wherein receiving the user-input of a desired stimulation response comprises providing, by the processor, a user interface wherein a user can indicate, for each candidate stimulation site, a stimulation objective.

9. The method of claim 8, wherein the stimulation objective indicates an increase in neural activity or a reduction in neural activity.

10. The method of claim 1, receiving the indication of the indirect neuromodulation responses for the candidate stimulation sites comprises
performing a neuromodulation at at least one of the candidate stimulation sites; and
recording a neuromodulation response occurring at at least one of the candidate stimulation sites.

11. The method of claim 10, wherein performing the neuromodulation comprises performing a plurality of neuromodulations at at least one of the candidate stimulation sites using a plurality of different stimulation settings and
wherein recording the neuromodulation response comprises recording a neuromodulation response, for each of the plurality of different stimulation settings, occurring at at least one of the candidate stimulation sites.

12. The method of claim 11, wherein determining or receiving the electrode neuromodulation settings comprises determining the electrode neuromodulation settings based on the recorded neuromodulation responses.

* * * * *